United States Patent [19]

Parl et al.

[11] Patent Number: 4,976,270
[45] Date of Patent: Dec. 11, 1990

[54] APPARATUS FOR CONTINUOUSLY SAMPLING PLASMA

[75] Inventors: Fritz F. Parl, Nashville, Tenn.; Charles A. Bradley, Lubbock, Tex.; Herman Benge, Brentwood; David L. Black, Hendersonville, both of Tenn.

[73] Assignee: Vanderbilt University, Nashville, Tenn.

[21] Appl. No.: 329,801

[22] Filed: Mar. 28, 1989

[51] Int. Cl.$^5$ ............................................. A61B 5/00
[52] U.S. Cl. ..................................................... 128/760
[58] Field of Search .................... 128/760; 604/4–6

[56] References Cited

U.S. PATENT DOCUMENTS

| | | | |
|---|---|---|---|
| 2,137,132 | 11/1938 | Cooley | 128/276 |
| 3,802,432 | 4/1974 | Djerassi | 128/214 R |
| 3,848,592 | 11/1974 | Willock | 128/214 R |
| 4,063,554 | 12/1977 | Willock et al. | 604/5 |
| 4,098,275 | 7/1978 | Consalvo | 604/5 |
| 4,559,034 | 12/1985 | Kirita et al. | 604/52 |
| 4,614,513 | 9/1986 | Bensinger | 604/6 |
| 4,619,639 | 10/1986 | Nose et al. | 604/5 |
| 4,639,243 | 1/1987 | Schmidt et al. | 604/6 |
| 4,666,426 | 5/1987 | Aigner | 604/5 |
| 4,675,004 | 1/1987 | Hadford et al. | 604/4 |

*Primary Examiner*—Max Hinenburg
*Attorney, Agent, or Firm*—Tilton, Fallon, Lungmus

[57] ABSTRACT

A method and apparatus for continuously sampling plasma are disclosed. The method of the present invention comprises removing blood from the patient, separating a substantially small portion of plasma, and returning the blood to the patient. The removing, separating, and returning steps are performed continuously and simultaneously with each other. The apparatus of the present invention relates to a double-lumen cannula or venipuncture needle for the removal and returning of blood to the patient at the same site.

4 Claims, 3 Drawing Sheets

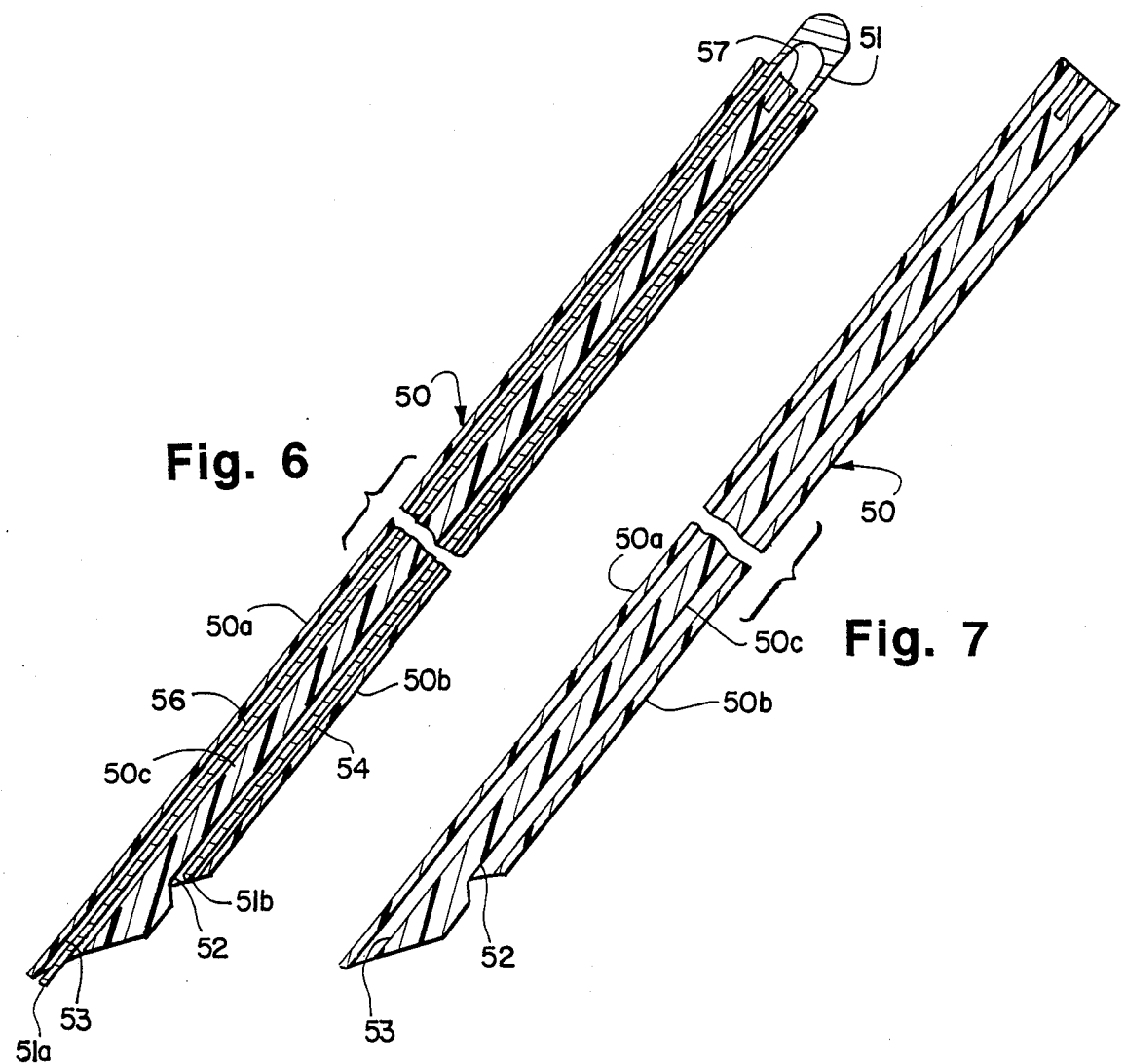
Fig. 6
Fig. 7
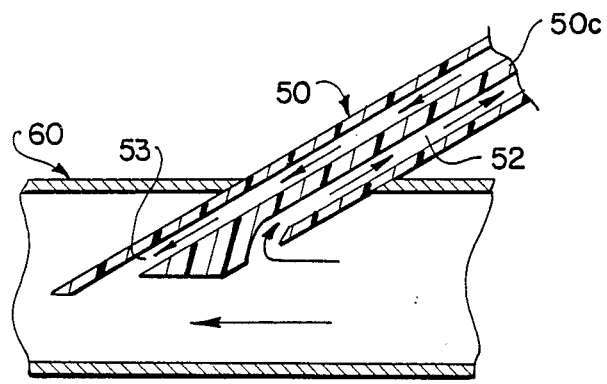
Fig. 8

APPARATUS FOR CONTINUOUSLY SAMPLING PLASMA

BACKGROUND AND PRIOR ART

The present invention relates to a method and apparatus for continuously sampling plasma.

To analyze the various chemical properties of constituents contained in the blood, it is necessary that a volume of blood be extracted from the patient. In conventional practice, the whole blood is separated by centrifugation into cellular matter and plasma or serum. Chemical analysis is then performed on plasma or serum while the blood cells are discarded. Thus, repeated chemical analysis is associated with considerable loss of whole blood and blood cells. Frequent blood collections for diagnostic chemical analysis may cause anemia in severely ill, hospitalized patients, thereby worsening the clinical condition.

The prior art discloses several methods by which blood can be withdrawn and returned to the body. The blood can be withdrawn from an artery and returned through a vein by means of two separate surgical implantations. Dual venipuncture devices also require two separate needles, the second one (the outflow needle) being inserted into a different vein downstream, and placed in the same direction as the flow of blood. The duplex needle of U.S. Pat. No. 2,137,132 has a dual tubular construction, but the two tubes merge within the needle. Blood cannot be withdrawn and returned through the same needle. Instead, the flow of blood described in U.S. Pat. No. 2,137,132 requires two separate needles.

The dual flow cannula set of Consalvo U.S. Pat No. 4,098,275 has entry and exit apertures spaced substantially apart (1.1 inch) to avoid mixing of toxic blood components during hemodialysis of patients with renal failure. The 1.1 inch-distance between the apertures of the cannula requires positioning of the blood-intake aperture on the side of the cannula. This, in turn, necessitates shielding of the intake aperture to prevent collapse of the adjacent blood vessel wall over the aperture with subsequent blockage of blood flow upon attempts to withdraw blood. The high volume blood flow during hemodialysis is accommodated by a #15 gauge (0.072 in. O.D.) needle. Placing two #15 gauge needles side-by-side creates a cannula of substantial size which requires surgical exposure of a large blood vessel for placement. Finally, the rigid, metallic cannula poses a constant risk for vascular injury and penetration thereby making prolonged intravascular placement of the cannula impractical.

U.S. Pat. No. 3,848,592 discloses a blood pump system used in dialysis with a single hypodermic needle with a v-shaped neck used for withdrawing and returning blood to the patient. However, in the system, separate valving means are necessary for changing the direction of blood flow.

U.S. Pat No. 4,614,513 relates to a method and apparatus for removing immunoreactive substances from blood. The treatment requires complete physical separation of blood cells and plasma in separate compartments. Addition of an anticoagulant to the system is essential to prevent coagulation of the separated blood cells. Therefore, U.S. Pat. No. 4,614,513 is concerned with a blood treatment system which in operation would not be closed.

In other conventional procedures for removal of blood from the patient, the line usually contains a filter and pumping means and means for sampling the blood from the line. In this regard, the system must be opened for removal of the sample of blood so that the blood may be analyzed or that the plasma can be separated. An anticoagulant is usually added to the blood to prevent the blood from clotting.

Due to the problems associated with the use of anticoagulants or other agents, there is a need for the sampling of blood and, more particularly, plasma analysis for diagnostic purposes, wherein the system is closed. The closed system has less reliance on the use of anticoagulants because of the quick transit time of the blood through the system.

SUMMARY OF THE INVENTION

The present invention provides a method and apparatus for continuously sampling plasma in a closed system for diagnostic purposes. The whole blood is removed from the patient and the plasma separated from the removed blood wherein the removed cellular elements of the blood are returned to the patient at the same site. The removing, separating, and returning steps of the process are performed substantially continuously and simultaneously with each other.

Further, the present invention provides a venipuncture cannula consisting of two components (a) a double-lumen body of a resilient material, i.e. plastic, and (b) a solid stainless steel core within each passageway of said double-lumen body. After penetrating the skin by the piercing points of the rigid core and positioning the needle in a blood vessel, the rigid core is retracted thereby allowing prolonged placement of the double-lumen cannula in the vessel without injuring the vessel wall due to the presence of the resilient plastic sheath contacting the vessel wall. After removal of the metal core, flexible tubing may be connected to the cannula for transporting blood. The passageways are separate and distinct in the cannula for blood leaving and returning to the blood vessel.

In another aspect, the present invention provides a loop of sterile tubing which is filled with Ringer's solution or isotonic saline to be connected to the inlet and outlet ports of the double-lumen cannula. Therefore, by means of a pump, the present invention provides a system for unidirectional flow of blood from the patient through the inflow lumen into the tubing and back through the outflow lumen of the double-lumen sheath at the same vascular site into the patient.

More particularly, the present invention provides a method and apparatus for continuously sampling plasma for diagnostic purposes in a system closed with reference to cellular components of blood. A substantially small portion of plasma is removed from the blood by filtration through a non-wettable plastic membrane filter in the side of the tubing thereby permitting collection of the plasma in collecting means, preferably on solid phase reagent strips brought into immediate contact with the tubing, while retaining the essential body of plasma and all blood cells in the tubing. The various steps of the process, including removal of blood from the patient, separation of a small portion of plasma from the blood, and returning the essential body of blood to the patient are performed substantially continuously and simultaneously with each other, thereby eliminating the need for centrifugation, anti-coagulation, blood replacement and repeated needle puncture of the patient.

In another aspect, the present invention provides a system for diagnostic purposes by removing blood from the patient, separating the plasma and returning the blood to the patient. The system comprises means for removing a continuous flow of blood from the patient, means for continuously separating the removed blood into plasma for further diagnostic purposes, means to collect the plasma and means for returning the blood and remaining component parts thereof to the patient at the same vascular site within a closed system where there is no introduction of air or other contaminants to the bloodstream without the need for an anticoagulant to be present in the system.

In yet another aspect, the present invention provides a venipuncture cannula consisting of the following components: (a) a one piece, U-shaped rigid core; (b) a body made of flexible material having proximal and distal ends with inflow and outflow lumina, said core engaging each lumen with the looped end of the core positioned at the proximal end of the body that may be connected to flexible tubing. The two piercing points of the rigid core are inserted into the blood vessel to the extent that the body of the cannula contacts the walls of the blood vessels. After penetrating the skin by the piercing tips of the rigid core and positioning the needle in a blood vessel, the rigid core is retracted thereby allowing prolonged placement of the double-lumen cannula in the vessel without injuring the vessel wall due to the presence of the resilient plastic body contacting the vessel wall. Plastic tubing may then be connected to the proximal end of the cannula for transporting blood to the separation and collection means or cartridge and returning to the patient. Therefore, blood can be removed from the patient, passed through the tubing where it is pumped, filtered, and subjected to separation of plasma for diagnostic purposes and returned in the tubing to the vascular site through the outflow lumen to the blood vessel. The two-component system offers the advantage of allowing prolonged placement of the double-lumen which is made from resilient material, i.e., plastic or other suitable material in the blood vessel without injuring the vessel wall.

BRIEF DESCRIPTION OF THE DRAWINGS

FIG. 6 is a cross-sectional view of the venipuncture cannula of the present invention;

FIG. 7 is a cross-sectional view of the venipuncture cannula of the present invention with the hollow metal sleeve removed;

FIG. 8 is a cross-section of the venipuncture cannula inserted into a blood vessel.

DETAILED DESCRIPTION OF THE INVENTION

Figure 1:
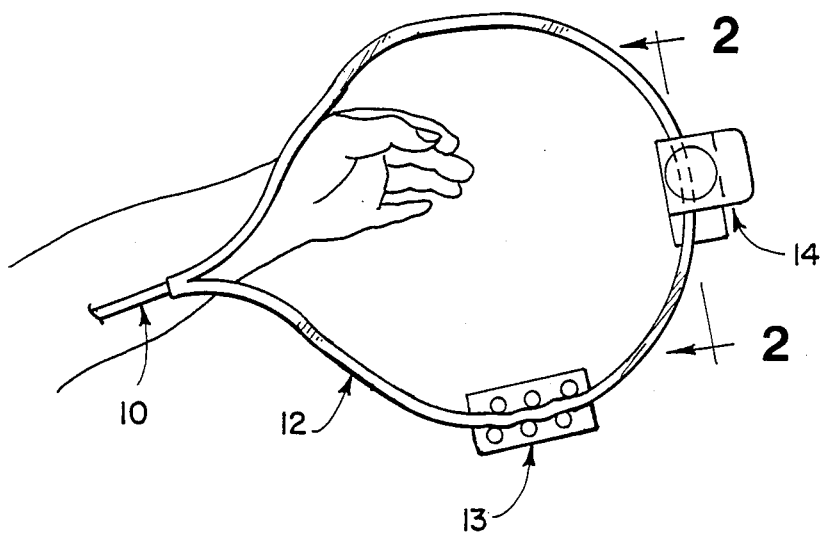
FIG. 1 is a schematic diagram of an apparatus for removing and returning blood to a patient that may be used for carrying out the present invention.

Referring now more particularly to FIG. 1, which illustrates one preferred apparatus for continuously sampling plasma in a closed system for diagnostic purposes, is fluid connection 10 in the form of a venipuncture needle comprising a cannula formed of flexible material having inflow and outflow lumina that reduces trauma to the blood vessel wall. The needle 10 is inserted into a blood vessel in one arm 11 of the patient for withdrawing blood and the subsequent separation of plasma components for diagnostic purposes. A blood flow path is formed when the blood is pumped through flexible conduit 12 by pumping means 13. Pumping means 13 may be any conventional motor-driven pump, such as rotary, tandem diaphragm, piston or variable speed pump to provide the desired rate of blood flow from the patient and delivery of blood to collection means or cartridge 14 and return to needle 10.

Figure 2:
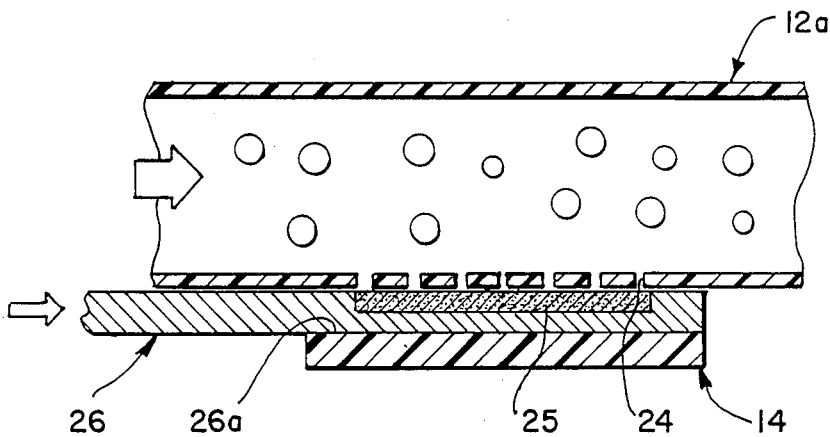
FIG. 2 is a sectional diagram of a collection device taken from line 2—2 of FIG. 1.
Figure 3:
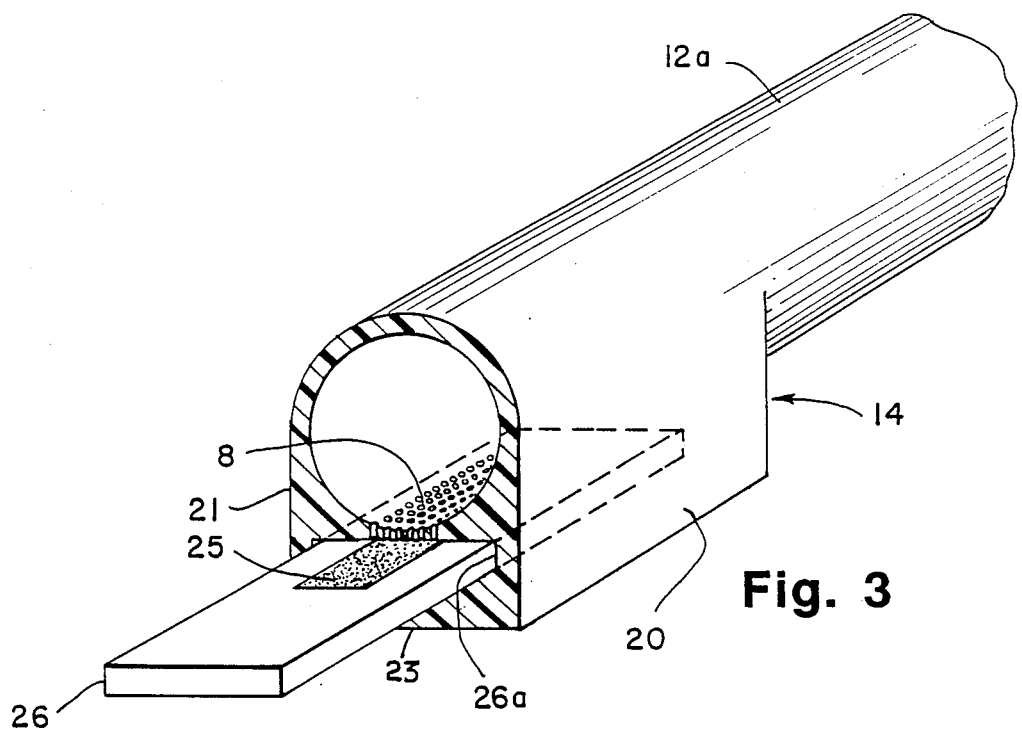
FIG. 3 is a perspective view of a collection device of the present invention, including a dry chemical diagnostic slide.

The collection means or cartridge 14 may be any device capable of separating plasma components from the blood in a closed system, that is, a system closed from the entrance of air or other contaminants but still being removable and preferably disposable. Collection means 14 as shown in FIGS. 2 and 3 comprises a hollow container having sidewalls 20 and 21 with bottom member 23 that is molded into conduit 12a and collection means 14. The darkened arrow in FIG. 2 denotes direction of blood flow. The circles represent cellular blood components. Conduit 12a and collection means 14 may be prepared from flexible plastic material such as Tygon ® tubing on the tube. Flexible conduit 12 engages molded conduit 12a in the blood flow path before and after collection means 14. Membrane line 24 comprises minute openings which act as conduits for filtering plasma from the blood. The filter or membrane may be any non-wettable plastic resin, preferably polycarbonate resin. Pore size should be any size effective to retain cellular blood components in the blood flow path within conduit 12 but allow plasma to be separated. Preferred pore size is about 1.0 μm but the pore size may range from about 0.5 μm to about 1.5 μm.

The plasma is preferably drawn to a dry chemical system for a solid phase chemical analysis, preferably a multilayer film comprising dry reagents. The plasma is drawn into reagent strip 25 on removable card 26 by the peripheral pressure exerted by the passing of the blood in its flow path through conduit 12. The arrow of FIG. 2 also denotes the direction for inserting card 26 in slot 26a in collection means 14. In a preferred embodiment, plasma migrates through membrane 24 in conduit 12 onto reagent strip 25 for analysis. The reagent strip 25 engages membrane 24 in a manner to be substantially airtight so that the system remains closed and the blood does not coagulate or become contaminated. Reagent strip 25 contains a solid phase reagent containing a matrix into which are impregnated those reagents for a given chemical determination of the plasma. Card 26 containing reagent strip 25 can be easily removed from slot 26a for analysis of the sample and a new card can be inserted in slot 26a in collection means 14.

Well-known methodologies are employed. For example, the layered-coating chemical system described by T. Shire in an article entitled "Development of a Layered-Coating Technology for Clinical Chemistry" in Clinical Chemistry, Vol. 16, No. 2, pp. 147-155 (1983), can function in the present invention. Several manufacturers of clinical chemistry products supply dry chemistry, solid support systems that are considered to be conventional in the art and may be utilized with the present invention. For example, Eastman Kodak Company, Rochester, New York, manufacturers slides with dry, multi-layered chemicals coated on a polyester support. The support may be used to measure the following analytes: sodium, potassium chloride, carbon dioxide, calcium, ammonia, urea nitrogen, creatinine, uric acid, glucose, bilirubin, cholesterol, triglycerides, albumin, total protein, and enzymes such as alanine aminotransferase, alkaline phosphatase, gamma glutamyltransferase, and lactacte dehydrogenase. Hybritech, Inc., San Diego, Calif., manufactures a solid phase assay for human choriogonadrotropin (HCG). Syntex Medical Diagnostics, Palo Alto, Calif., manufactures an assay for determining the level of a drug, theophyllin, using a solid phase paper strip. Any conventional dry chemical system for assaying analytes may be used in the system of the present invention.

Figure 4:
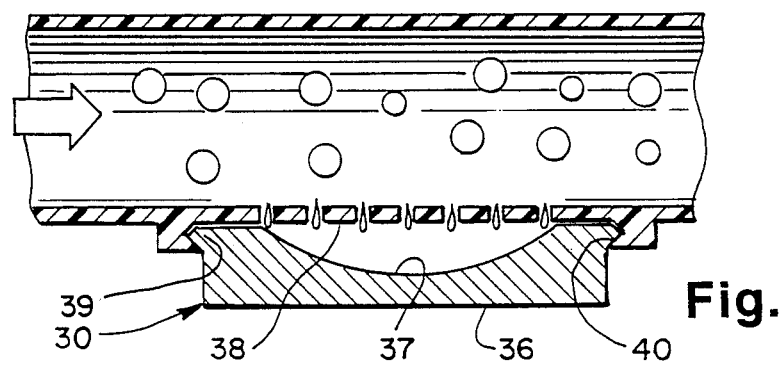
FIG. 4 is a cross-sectional view of another embodiment of a collection device taken from line 2—2 of FIG. 1, including a pool of saline.

An alternate embodiment for collection means is shown in FIG. 4. Collection means 30 comprises a hollow container having sidewalls 31 and 32 and front and back walls 33 and 34 with bottom member 35 connected thereto. Collection member 36 defines the interior of the collection means with a concave surface 37 for collecting plasma from the blood in conduit 12. Blood is shown by circles in the drawing with an arrow indicating direction of flow. Filter plate or membrane 38 in line 12 comprises minute openings which act as conduits for filtering plasma from the blood. As in the other embodiment, the filter or membrane 38 may be any non-wettable plastic resin. Pore size is as previously stated, any size effective to retain cellular blood components in the blood flow path within conduit 12 but allow plasma to be separated. Preferred pore size is about 1.0 $\mu$m, however, the pore size may range from about 0.5 $\mu$m to about 1.5 $\mu$m. Concave surface 25 may contain a fluid such as saline or other compatible fluid for collecting plasma.

Figure 5:
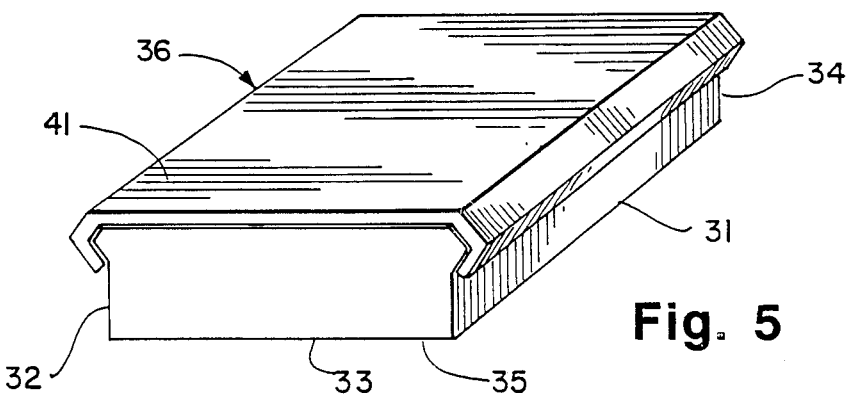
FIG. 5 is a perspective view of the alternate collection devices for collecting plasma.

Collection means 30 can be fitted into conduit 12 by laterally extending ridges 39 of collection member 36 which fit engagingly into grooves 40 in line 12. After completion of a sample, collection means 30 is pushed from groves 40 and covered with lid 41 so that collection means 30 may be transported to a suitable area for plasma analysis and diagnosis as shown in FIG. 5. Plasma may be removed from the area defined by concave surface 37 containing a compatible solution after a period of about 20-30 minutes by a micro pipette or similar means.

After removal of collection means 30 from line 12, a second collection means is inserted in grooves 40 for collecting plasma.

As shown in FIG. 6, the venipuncture needle or cannula 50, which is used for facile insertion into a blood vessel, consists of two components: a U-shaped or looped steel core 51, which engages blood inflow lumen 52 through which blood is circulated into collection means, and outlet lumen 53 through which blood returns to the vessel. The lumina are substantially parallel extending from the distal to proximal ends of the cannula and within elongated tubular walls 50a and 50b of the cannula. The lumina are separated by septum 50c. Core 51 contains legs of unequal length with piercing points 51a and 51b. Leg 54 engages inflow lumen 52 and is shielded by it. Leg 56 is longer than leg 54 and engages outflow lumen 53 in its entire length and protrudes slightly from its distal end. This provides for facile insertion of the cannula into a blood vessel. The body of the venipuncture needle may be made from a flexible material such as Tygon ® tubing or other suitable plastic material. The cannula or venipuncture needle has a pointed forward end where all components are inserted into a blood vessel. Upon insertion, the U-shaped rigid core may be withdrawn from its distal end, allowing the resilient, flexible cannula in the blood vessel. The flexible material can be retained in the blood vessel for long periods of time and reduces trauma to the vessel. At that time, conduit 14, which is split at its input end into two tubes, each of which may engage the notched portion 57 at the proximal end of cannula 50. FIG. 7 shows a sectional view of the venipuncture or cannula needle with the metal core 51 removed to better define the lumina or channels 52 and 53. Accordingly, FIG. 8 shows a sectional view of venipuncture or cannula needle 50 inserted through a wall of a blood vessel 60.

Further, downstream from the collection means in line 12 there may be inserted a port for placing therapeutic agents in the system.

Some of the components of the system, i.e. tubing collection means, cannula, etc., may be made from inexpensive materials and are disposable.

In the method and apparatus of the present invention, cellular blood components remain in the vasculature. The method and apparatus greatly shorten the analysis time of the plasma constituents of blood and allows continuous sampling of plasma for repeatedly monitoring blood constituents.

Obvious modifications and variations in the present invention are possible in light of the aforementioned teachings. It is, therefore, to be understood that within the pending claims the invention may be practiced otherwise than as specifically described.

What is claimed is:

1. An apparatus for continuously sampling plasma in a closed system for a patient comprising:
   means for removing a continuous flow of blood from a patient at a site on the patient and for returning removed blood to the patient at said site;
   means for creating a blood flow path including pumping means and tubing means, said tubing means communicating between said means for removing and returning blood, and said pumping means; and
   means for separating the plasma component from the removed blood in said blood flow path;
   said removal and return means comprising a cannula body formed of flexible material having proximal and distal ends; said body having on outflow lumen and inflow lumen extending from said proximal end to said distal end; said body also having a rigid, one-piece removable core extending the length of and within both lumina from the proximal to distal ends and being looped at the proximal end, said core being utilized to insert said apparatus into a blood vessel.

2. An apparatus for continuously sampling plasma in a closed system from a patient comprising:
   cannula means for removing a continuous flow of blood from a patient at a site on the patient and for returning removed blood to the patient at said site;
   means for creating a blood flow path including pumping means and tubing means, said tubing means defining a closed loop leading from and returning to said cannula means, with said pumping means being located along said closed loop;

separating means for separating the plasma component from the removed blood in said blood flow path, said separating means comprising a filtering membrane wall portion of said tubing means having pores of a size sufficiently small to retain cellular blood components within said tubing means while allowing plasma to pass therethrough; and collecting means comprising a chamber communicating with said tubing means through said filtering membrane wall portion and having a removable collecting member slidably received in said chamber for collecting and retaining a sample of plasma.

3. The apparatus of claim 2 in which said collecting member comprises a card for receiving said plasma, said card including a reagent strip containing a solid phase reagent for reaction with said plasma.

4. The apparatus of claim 2 in which said collecting member includes a concavity facing said filtering membrane wall portion for receiving and retaining a sample of said plasma.

* * * * *